US011959099B2

(12) United States Patent
Matsuzaki et al.

(10) Patent No.: US 11,959,099 B2
(45) Date of Patent: Apr. 16, 2024

(54) DELIVERY METHOD

(71) Applicants: Cell Guidance Systems Limited, Cambridge (GB); Yuka Matsuzaki, Sakyo-ku (JP); Hajime Mori, Sakyo-ku (JP)

(72) Inventors: Yuka Matsuzaki, Sakyo-ku (JP); Hajime Mori, Sakyo-ku (JP); Christian Pernstich, Cambridge (GB); Michael Howard Jones, Cambridge (GB)

(73) Assignees: Cell Guidance Systems Limited, Cambridge (GB); Yuka Matsuzakt, Sakyo-ku (JP); Hajime Mori, Sakyo-ku (JP)

(*) Notice: Subject to any disclaimer, the term of this patent is extended or adjusted under 35 U.S.C. 154(b) by 542 days.

(21) Appl. No.: 16/604,881

(22) PCT Filed: Apr. 11, 2018

(86) PCT No.: PCT/GB2018/000064
§ 371 (c)(1),
(2) Date: Oct. 11, 2019

(87) PCT Pub. No.: WO2018/189501
PCT Pub. Date: Oct. 18, 2018

(65) Prior Publication Data

US 2020/0277570 A1 Sep. 3, 2020

(30) Foreign Application Priority Data

Apr. 13, 2017 (GB) ..................................... 1705955

(51) Int. Cl.
*C12N 5/0793* (2010.01)
*A61K 38/18* (2006.01)
*C12N 15/86* (2006.01)

(52) U.S. Cl.
CPC .......... *C12N 5/0619* (2013.01); *A61K 38/185* (2013.01); *C12N 15/86* (2013.01); *C12N 2501/13* (2013.01)

(58) Field of Classification Search
None
See application file for complete search history.

(56) References Cited

U.S. PATENT DOCUMENTS 6,005,081 A * 12/1999 Burton .................. C07K 14/48 435/71.1
6,835,567 B1 * 12/2004 Sah ..................... C12N 5/0623 435/325

FOREIGN PATENT DOCUMENTS

WO WO-2014130449 A1 * 8/2014 ............ A61L 27/18
WO WO-2014130449 A1 8/2014
WO WO-2018189501 A2 10/2018

OTHER PUBLICATIONS

Skolnick (Trends Biotechnol. Jan. 2000;18(1):34-9) (Year: 2000).*
Burgess et al. (J. Cell Biol. 111:2129-2138, 1990) (Year: 1990).*
Miosge (Proc Natl Acad Sci US A. Sep. 15, 2015;112(37): E5189-98) (Year: 2015).*
Bork (Genome Research, 2000, 10:398-400) (Year: 2000).*
Nishishita (Biomaterials, 32: 3555-3563, 2011 (Year: 2011).*
Tayalia & Mooney "Controlled Growth Factory Delivery for Tissue Engineering" 2009, Advanced Materials, vol. 21: 3269-3285. (Year: 2009).*
Aloe et al. "Nerve growth factor: from teh early discoveries to the potential clinical use" (2012), J Translational Medicine, vol. 10-239: 1-15. (Year: 2012).*
"International Application No. PCT/GB2018/000064, International Search Report and Written Opinion dated Dec. 12, 2018", (dated Dec. 12, 2018), 12 pgs.
Altschul, S. F., "A protein alignment scoring system sensitive at all evolutionary distances", J Mol. Evol., Mar. 1993; 36(3):290-300 [abstract only], (Mar. 1993), 290-300.
Altschul, Stephen F., et al., "Basic Local Alignment Search Tool", J. Mol. Biol., 215(3), 403-410 (1990), (Oct. 5, 1990), 403-410.
Devereux, J., et al., "A comprehensive set of sequence analysis programs for the VAX", Nucleic Acids Research, Jan. 1, 19841; 12(1 Pt 1):387-395, (Jan. 11, 1984), 387-395.
Henikoff, Steven, et al., "Amino acid substitution matrices from protein blocks", Proc. Natl. Acad. Sci. USA, vol. 89, 10915-10919, (Nov. 1992), 10915-10919.
Ijiri, H., et al., "Structure-based targeting of bioactive proteins into cypovirus polyhedra and application to immobilized cytokines for mammalian cell culture", Biomaterials, vol. 30, No. 26, (Sep. 1, 2009), 4297-4308.
Karlin, Samuel, et al., "Applications and statistics for multiple high-scoring segments in molecular sequences", Proc. Natl. Acad. Sci. USA, vol. 90, 5873-5877, (Jun. 1993), 5873-5877.
Kotani, Eiji, et al., "Cell proliferation by silk gut incorporating FGF-2 protein microcrystals", Scientific Reports, vol. 5, No. 1, (Jun. 8, 2015), 10 pgs.

(Continued)

*Primary Examiner* — Teresa E Knight

(74) *Attorney, Agent, or Firm* — Schwegman Lundberg & Woessner, P.A.

(57) ABSTRACT

A method of altering cells comprising culturing them in a growth factor gradient, wherein said gradient is provided by a polyhedra delivery system (PODS) that releases the growth factor to set up the gradient.

18 Claims, 3 Drawing Sheets

Specification includes a Sequence Listing.

(56) References Cited

OTHER PUBLICATIONS

Mori, Hajime, et al., "Immobilization of Bioactive Fibroblast Growth Factor-2 into Cubic Proteinous Microcrystals (Bombyx mori Cypovirus Polyhedra) That Are Insoluble in a Physiological Cellular Environment", The Journal of Biological Chemistry vol. 282, No. 23, pp. 17289-17296, Jun. 8, 2007, (Jun. 8, 2007), 17289-17296.

Nishishita, Naoki, et al., "The use of leukemia inhibitory factor immobilized on virus-derived polyhedra to support the proliferation of mouse embryonic and induced pluripotent stem cells", Biomaterials, vol. 32, Issue 14 [abstract only], (May 2011), 3555-3563.

Shimabukuro, Junji, et al., "3D co-cultures of keratinocytes and melanocytes and cytoprotective effects on keratinocytes against reactive oxygen species by insect virus-derived protein microcrystals", Materials Science and Engineering, vol. 42 [abstract only], (May 15, 2014), 64-69.

* cited by examiner

Fig. 1 Construction of NGF polyhedra. Full-length and mature NGF (full NGF and mature NGF, respectively) were fused with either a H1 or VP3 tag, and each recombinant NGF fusion protein was encapsulated into polyhedra.

```
                                SEQUENCE LISTING


<160> NUMBER OF SEQ ID NOS: 16

<210> SEQ ID NO 1
<211> LENGTH: 223
<212> TYPE: PRT
<213> ORGANISM: Homo sapiens

<400> SEQUENCE: 1

Glu Pro His Ser Glu Ser Asn Val Pro Ala Gly His Thr Ile Pro Gln
1               5                   10                  15

Val His Trp Thr Lys Leu Gln His Ser Leu Asp Thr Ala Leu Arg Arg
            20                  25                  30

Ala Arg Ser Ala Pro Ala Ala Ala Ile Ala Ala Arg Val Ala Gly Gln
        35                  40                  45

Thr Arg Asn Ile Thr Val Asp Pro Arg Leu Phe Lys Lys Arg Arg Leu
    50                  55                  60

Arg Ser Pro Arg Val Leu Phe Ser Thr Gln Pro Pro Arg Glu Ala Ala
65                  70                  75                  80

Asp Thr Gln Asp Leu Asp Phe Glu Val Gly Gly Ala Ala Pro Phe Asn
                85                  90                  95

Arg Thr His Arg Ser Lys Arg Ser Ser Ser His Pro Ile Phe His Arg
            100                 105                 110

Gly Glu Phe Ser Val Cys Asp Ser Val Ser Val Trp Val Gly Asp Lys
        115                 120                 125

Thr Thr Ala Thr Asp Ile Lys Gly Lys Glu Val Met Val Leu Gly Glu
    130                 135                 140

Val Asn Ile Asn Asn Ser Val Phe Lys Gln Tyr Phe Phe Glu Thr Lys
145                 150                 155                 160

Cys Arg Asp Pro Asn Pro Val Asp Ser Gly Cys Arg Gly Ile Asp Ser
                165                 170                 175

Lys His Trp Asn Ser Tyr Cys Thr Thr Thr His Thr Phe Val Lys Ala
            180                 185                 190

Leu Thr Met Asp Gly Lys Gln Ala Ala Trp Arg Phe Ile Arg Ile Asp
        195                 200                 205

Thr Ala Cys Val Cys Val Leu Ser Arg Lys Ala Val Arg Arg Ala
    210                 215                 220


<210> SEQ ID NO 2
<211> LENGTH: 120
<212> TYPE: PRT
<213> ORGANISM: Homo sapiens

<400> SEQUENCE: 2

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
                85                  90                  95

Ala Ala Trp Arg Phe Ile Arg Ile Asp Thr Ala Cys Val Cys Val Leu
```

```
            100                 105                 110

Ser Arg Lys Ala Val Arg Arg Ala
        115                 120


<210> SEQ ID NO 3
<211> LENGTH: 30
<212> TYPE: PRT
<213> ORGANISM: Artificial Sequence
<220> FEATURE:
<223> OTHER INFORMATION: A synthetic H1-tag sequence

<400> SEQUENCE: 3

Met Ala Asp Val Ala Gly Thr Ser Asn Arg Asp Phe Arg Gly Arg Glu
1               5                   10                  15

Gln Arg Leu Phe Asn Ser Glu Gln Tyr Asn Tyr Asn Asn Ser
            20                  25                  30


<210> SEQ ID NO 4
<211> LENGTH: 53
<212> TYPE: PRT
<213> ORGANISM: Artificial Sequence
<220> FEATURE:
<223> OTHER INFORMATION: A synthetic VP3-tag sequence

<400> SEQUENCE: 4

Ala Phe Asn Ser Gln Arg Arg Ser His Thr Leu Arg Leu Leu Gly Pro
1               5                   10                  15

Phe Gln Tyr Phe Asn Phe Ser Glu Thr Asp Arg Gly His Pro Leu Phe
            20                  25                  30

Arg Leu Pro Leu Lys Tyr Pro Ser Lys Ala Ile Pro Ala Asp Glu Leu
        35                  40                  45

Ile Asp Asn Leu His
    50


<210> SEQ ID NO 5
<211> LENGTH: 672
<212> TYPE: DNA
<213> ORGANISM: Homo sapiens

<400> SEQUENCE: 5

gaaccacact cagagagcaa tgtccctgca ggacacacca tcccccaagt ccactggact      60

aaacttcagc attcccttga cactgccctt cgcagagccc gcagcgcccc ggcagcggcg     120

atagctgcac gcgtggcggg gcagacccgc aacattactg tggaccccag gctgtttaaa     180

aagcggcgac tccgttcacc ccgtgtgctg tttagcaccc agcctccccg tgaagctgca     240

gacactcagg atctggactt cgaggtcggt ggtgctgccc ccttcaacag gactcacagg     300

agcaagcggt catcatccca tcccatcttc cacaggggcg aattctcggt gtgtgacagt     360

gtcagcgtgt gggttgggga taagaccacc gccacagaca tcaagggcaa ggaggtgatg     420

gtgttgggag aggtgaacat taacaacagt gtattcaaac agtacttttt tgagaccaag     480

tgccgggacc caaatcccgt tgacagcggg tgccggggca ttgactcaaa gcactggaac     540

tcatattgta ccacgactca cacctttgtc aaggcgctga ccatggatgg caagcaggct     600

gcctggcggt ttatccggat agatacggcc tgtgtgtgtg tgctcagcag gaaggctgtg     660

agaagagcct ga                                                          672


<210> SEQ ID NO 6
<211> LENGTH: 363
<212> TYPE: DNA
```

<213> ORGANISM: Homo sapiens

<400> SEQUENCE: 6
tcatcatccc atcccatctt ccacaggggc gaattctcgg tgtgtgacag tgtcagcgtg 60
tgggttgggg ataagaccac cgccacagac atcaagggca aggaggtgat ggtgttggga 120
gaggtgaaca ttaacaacag tgtattcaaa cagtactttt ttgagaccaa gtgccgggac 180
ccaaatcccg ttgacagcgg gtgccggggc attgactcaa agcactggaa ctcatattgt 240
accacgactc acacctttgt caaggcgctg accatggatg gcaagcaggc tgcctggcgg 300
tttatccgga tagatacggc ctgtgtgtgt gtgctcagca ggaaggctgt gagaagagcc 360
tga 363

<210> SEQ ID NO 7
<211> LENGTH: 268
<212> TYPE: PRT
<213> ORGANISM: Artificial Sequence
<220> FEATURE:
<223> OTHER INFORMATION: A synthetic H1-NGF (full length) fusion protein sequence

<400> SEQUENCE: 7

Met Ala Asp Val Ala Gly Thr Ser Asn Arg Asp Phe Arg Gly Arg Glu
1 5 10 15

Gln Arg Leu Phe Asn Ser Glu Gln Tyr Asn Tyr Asn Asn Ser Lys Asn
20 25 30

Ser Arg Pro Ser Thr Ser Leu Tyr Lys Lys Ala Gly Ser Glu Pro His
35 40 45

Ser Glu Ser Asn Val Pro Ala Gly His Thr Ile Pro Gln Val His Trp
50 55 60

Thr Lys Leu Gln His Ser Leu Asp Thr Ala Leu Arg Arg Ala Arg Ser
65 70 75 80

Ala Pro Ala Ala Ala Ile Ala Ala Arg Val Ala Gly Gln Thr Arg Asn
85 90 95

Ile Thr Val Asp Pro Arg Leu Phe Lys Lys Arg Arg Leu Arg Ser Pro
100 105 110

Arg Val Leu Phe Ser Thr Gln Pro Pro Arg Glu Ala Ala Asp Thr Gln
115 120 125

Asp Leu Asp Phe Glu Val Gly Gly Ala Ala Pro Phe Asn Arg Thr His
130 135 140

Arg Ser Lys Arg Ser Ser Ser His Pro Ile Phe His Arg Gly Glu Phe
145 150 155 160

Ser Val Cys Asp Ser Val Ser Val Trp Val Gly Asp Lys Thr Thr Ala
165 170 175

Thr Asp Ile Lys Gly Lys Glu Val Met Val Leu Gly Glu Val Asn Ile
180 185 190

Asn Asn Ser Val Phe Lys Gln Tyr Phe Phe Glu Thr Lys Cys Arg Asp
195 200 205

Pro Asn Pro Val Asp Ser Gly Cys Arg Gly Ile Asp Ser Lys His Trp
210 215 220

Asn Ser Tyr Cys Thr Thr Thr His Thr Phe Val Lys Ala Leu Thr Met
225 230 235 240

Asp Gly Lys Gln Ala Ala Trp Arg Phe Ile Arg Ile Asp Thr Ala Cys
245 250 255

Val Cys Val Leu Ser Arg Lys Ala Val Arg Arg Ala
260 265

<210> SEQ ID NO 8
<211> LENGTH: 807
<212> TYPE: DNA
<213> ORGANISM: Artificial Sequence
<220> FEATURE:
<223> OTHER INFORMATION: A synthetic H1-NGF (full length) fusion protein sequence

<400> SEQUENCE: 8
atggcagacg tagcaggaac aagtaaccga gactttcgcg gacgcgaaca aagactattc 60
aatagcgaac aatacaacta taacaacagc aagaattcta gaccatcaac aagtttgtac 120
aaaaaagcag gctccgaacc acactcagag agcaatgtcc ctgcaggaca caccatcccc 180
caagtccact ggactaaact tcagcattcc cttgacactg cccttcgcag agcccgcagc 240
gccccggcag cggcgatagc tgcacgcgtg gcggggcaga cccgcaacat tactgtggac 300
cccaggctgt ttaaaaagcg gcgactccgt tcaccccgtg tgctgtttag cacccagcct 360
ccccgtgaag ctgcagacac tcaggatctg gacttcgagg tcggtggtgc tgccccccttc 420 aacaggactc acaggagcaa gcggtcatca tcccatccca tcttccacag gggcgaattc 480
tcggtgtgtg acagtgtcag cgtgtgggtt ggggataaga ccaccgccac agacatcaag 540
ggcaaggagg tgatggtgtt gggagaggtg aacattaaca acagtgtatt caaacagtac 600
ttttttgaga ccaagtgccg ggacccaaat cccgttgaca gcgggtgccg gggcattgac 660
tcaaagcact ggaactcata ttgtaccacg actcacacct ttgtcaaggc gctgaccatg 720
gatggcaagc aggctgcctg gcggtttatc cggatagata cggcctgtgt gtgtgtgctc 780
agcaggaagg ctgtgagaag agcctga 807

<210> SEQ ID NO 9
<211> LENGTH: 165
<212> TYPE: PRT
<213> ORGANISM: Artificial Sequence
<220> FEATURE:
<223> OTHER INFORMATION: A synthetic H1-NGF fusion protein sequence

<400> SEQUENCE: 9

Met Ala Asp Val Ala Gly Thr Ser Asn Arg Asp Phe Arg Gly Arg Glu
1               5                   10                  15

Gln Arg Leu Phe Asn Ser Glu Gln Tyr Asn Tyr Asn Asn Ser Lys Asn
            20                  25                  30

Ser Arg Pro Ser Thr Ser Leu Tyr Lys Lys Ala Gly Ser Ser Ser Ser
        35                  40                  45

His Pro Ile Phe His Arg Gly Glu Phe Ser Val Cys Asp Ser Val Ser
    50                  55                  60

Val Trp Val Gly Asp Lys Thr Thr Ala Thr Asp Ile Lys Gly Lys Glu
65                  70                  75                  80

Val Met Val Leu Gly Glu Val Asn Ile Asn Asn Ser Val Phe Lys Gln
                85                  90                  95

Tyr Phe Phe Glu Thr Lys Cys Arg Asp Pro Asn Pro Val Asp Ser Gly
            100                 105                 110

Cys Arg Gly Ile Asp Ser Lys His Trp Asn Ser Tyr Cys Thr Thr Thr
        115                 120                 125

His Thr Phe Val Lys Ala Leu Thr Met Asp Gly Lys Gln Ala Ala Trp
    130                 135                 140

Arg Phe Ile Arg Ile Asp Thr Ala Cys Val Cys Val Leu Ser Arg Lys
145                 150                 155                 160

```
Ala Val Arg Arg Ala
                165


<210> SEQ ID NO 10
<211> LENGTH: 498
<212> TYPE: DNA
<213> ORGANISM: Artificial Sequence
<220> FEATURE:
<223> OTHER INFORMATION: A synthetic H1-NGF fusion protein sequence

<400> SEQUENCE: 10

atggcagacg tagcaggaac aagtaaccga gactttcgcg gacgcgaaca aagactattc      60

aatagcgaac aatacaacta taacaacagc aagaattcta gaccatcaac aagtttgtac     120

aaaaaagcag gctcctcatc atcccatccc atcttccaca ggggcgaatt ctcggtgtgt     180

gacagtgtca gcgtgtgggt tggggataag accaccgcca cagacatcaa gggcaaggag     240

gtgatggtgt tgggagaggt gaacattaac aacagtgtat tcaaacagta ctttttttgag    300

accaagtgcc gggacccaaa tcccgttgac agcgggtgcc ggggcattga ctcaaagcac     360

tggaactcat attgtaccac gactcacacc tttgtcaagg cgctgaccat ggatggcaag     420

caggctgcct ggcggtttat ccggatagat acggcctgtg tgtgtgtgct cagcaggaag     480

gctgtgagaa gagcctga                                                   498


<210> SEQ ID NO 11
<211> LENGTH: 291
<212> TYPE: PRT
<213> ORGANISM: Artificial Sequence
<220> FEATURE:
<223> OTHER INFORMATION: A synthetic NGF-VP3 (full length) fusion
      protein sequence

<400> SEQUENCE: 11

Met Glu Pro His Ser Glu Ser Asn Val Pro Ala Gly His Thr Ile Pro
1               5                   10                  15

Gln Val His Trp Thr Lys Leu Gln His Ser Leu Asp Thr Ala Leu Arg
            20                  25                  30

Arg Ala Arg Ser Ala Pro Ala Ala Ala Ile Ala Ala Arg Val Ala Gly
        35                  40                  45

Gln Thr Arg Asn Ile Thr Val Asp Pro Arg Leu Phe Lys Lys Arg Arg
    50                  55                  60

Leu Arg Ser Pro Arg Val Leu Phe Ser Thr Gln Pro Pro Arg Glu Ala
65                  70                  75                  80

Ala Asp Thr Gln Asp Leu Asp Phe Glu Val Gly Gly Ala Ala Pro Phe
                85                  90                  95

Asn Arg Thr His Arg Ser Lys Arg Ser Ser Ser His Pro Ile Phe His
            100                 105                 110

Arg Gly Glu Phe Ser Val Cys Asp Ser Val Ser Val Trp Val Gly Asp
        115                 120                 125

Lys Thr Thr Ala Thr Asp Ile Lys Gly Lys Glu Val Met Val Leu Gly
    130                 135                 140

Glu Val Asn Ile Asn Asn Ser Val Phe Lys Gln Tyr Phe Phe Glu Thr
145                 150                 155                 160

Lys Cys Arg Asp Pro Asn Pro Val Asp Ser Gly Cys Arg Gly Ile Asp
                165                 170                 175

Ser Lys His Trp Asn Ser Tyr Cys Thr Thr Thr His Thr Phe Val Lys
            180                 185                 190
```

-continued

```
Ala Leu Thr Met Asp Gly Lys Gln Ala Ala Trp Arg Phe Ile Arg Ile
        195                 200                 205

Asp Thr Ala Cys Val Cys Val Leu Ser Arg Lys Ala Val Arg Arg Ala
    210                 215                 220

Met Gly Arg Lys Asn Met Phe His His Asp Gly Tyr Leu Leu Ala Phe
225                 230                 235                 240

Asn Ser Gln Arg Arg Ser His Thr Leu Arg Leu Leu Gly Pro Phe Gln
                245                 250                 255

Tyr Phe Asn Phe Ser Glu Thr Asp Arg Gly His Pro Leu Phe Arg Leu
            260                 265                 270

Pro Leu Lys Tyr Pro Ser Lys Ala Ile Pro Ala Asp Glu Leu Ile Asp
        275                 280                 285

Asn Leu His
    290


<210> SEQ ID NO 12
<211> LENGTH: 890
<212> TYPE: DNA
<213> ORGANISM: Artificial Sequence
<220> FEATURE:
<223> OTHER INFORMATION: A synthetic NGF-VP3 (full length) fusion
      protein sequence

<400> SEQUENCE: 12

atggaaccac actcagagag caatgtccct gcaggacaca ccatccccca agtccactgg      60

actaaacttc agcattccct tgacactgcc cttcgcagag cccgcagcgc cccggcagcg     120

gcgatagctg cacgcgtggc ggggcagacc cgcaacatta ctgtggaccc caggctgttt     180

aaaaagcggc gactccgttc accccgtgtg ctgtttagca cccagcctcc ccgtgaagct     240

gcagacactc aggatctgga cttcgaggtc ggtggtgctg ccccttcaa caggactcac      300

aggagcaagc ggtcatcatc ccatcccatc ttccacaggg gcgaattctc ggtgtgtgac     360

agtgtcagcg tgtgggttgg ggataagacc accgccacag acatcaaggg caaggaggtg     420

atggtgttgg gagaggtgaa cattaacaac agtgtattca aacagtactt ttttgagacc     480

aagtgccggg acccaaatcc cgttgacagc gggtgccggg gcattgactc aaagcactgg     540

aactcatatt gtaccacgac tcacaccttt gtcaaggcgc tgaccatgga tggcaagcag     600

gctgcctggc ggtttatccg gatagatacg gcctgtgtgt gtgtgctcag caggaaggct     660

gtgagaagag ccatgggtcg aaagaacatg tttcaccatg atgggtacct tctagctttc     720

aactcacaac gacgatcaca cacgttacga ctactagggc cttttcagta cttcaacttc     780

tccgagacag atagaggaca tccattattt cgcctacctc ttaagtatcc atcaaaagca     840

ataccagcag atgagttaat tgacaattta cactagtaac ggcggaataa                890


<210> SEQ ID NO 13
<211> LENGTH: 188
<212> TYPE: PRT
<213> ORGANISM: Artificial Sequence
<220> FEATURE:
<223> OTHER INFORMATION: A synthetic NGF-VP3 fusion protein sequence

<400> SEQUENCE: 13

Met Ser Ser Ser His Pro Ile Phe His Arg Gly Glu Phe Ser Val Cys
1               5                   10                  15

Asp Ser Val Ser Val Trp Val Gly Asp Lys Thr Thr Ala Thr Asp Ile
            20                  25                  30

Lys Gly Lys Glu Val Met Val Leu Gly Glu Val Asn Ile Asn Asn Ser
```

```
        35                  40                  45

Val Phe Lys Gln Tyr Phe Phe Glu Thr Lys Cys Arg Asp Pro Asn Pro
    50                  55                  60

Val Asp Ser Gly Cys Arg Gly Ile Asp Ser Lys His Trp Asn Ser Tyr
65                  70                  75                  80

Cys Thr Thr Thr His Thr Phe Val Lys Ala Leu Thr Met Asp Gly Lys
                85                  90                  95

Gln Ala Ala Trp Arg Phe Ile Arg Ile Asp Thr Ala Cys Val Cys Val
            100                 105                 110

Leu Ser Arg Lys Ala Val Arg Arg Ala Met Gly Arg Lys Asn Met Phe
        115                 120                 125

His His Asp Gly Tyr Leu Leu Ala Phe Asn Ser Gln Arg Arg Ser His
    130                 135                 140

Thr Leu Arg Leu Leu Gly Pro Phe Gln Tyr Phe Asn Phe Ser Glu Thr
145                 150                 155                 160

Asp Arg Gly His Pro Leu Phe Arg Leu Pro Leu Lys Tyr Pro Ser Lys
                165                 170                 175

Ala Ile Pro Ala Asp Glu Leu Ile Asp Asn Leu His
            180                 185


<210> SEQ ID NO 14
<211> LENGTH: 581
<212> TYPE: DNA
<213> ORGANISM: Artificial Sequence
<220> FEATURE:
<223> OTHER INFORMATION: A synthetic NGF-VP3 fusion protein sequence

<400> SEQUENCE: 14

atgtcatcat cccatcccat cttccacagg ggcgaattct cggtgtgtga cagtgtcagc     60

gtgtgggttg gggataagac caccgccaca gacatcaagg gcaaggaggt gatggtgttg    120

ggagaggtga acattaacaa cagtgtattc aaacagtact tttttgagac caagtgccgg    180

gacccaaatc ccgttgacag cgggtgccgg ggcattgact caaagcactg gaactcatat    240

tgtaccacga ctcacacctt tgtcaaggcg ctgaccatgg atggcaagca ggctgcctgg    300

cggtttatcc ggatagatac ggcctgtgtg tgtgtgctca gcaggaaggc tgtgagaaga    360

gccatgggtc gaaagaacat gtttcaccat gatgggtacc ttctagcttt caactcacaa    420

cgacgatcac acacgttacg actactaggg ccttttcagt acttcaactt ctccgagaca    480

gatagaggac atccattatt tcgcctacct cttaagtatc catcaaaagc aataccagca    540

gatgagttaa ttgacaattt acactagtaa cggcggaata a                        581


<210> SEQ ID NO 15
<211> LENGTH: 251
<212> TYPE: PRT
<213> ORGANISM: Bombyx mori

<400> SEQUENCE: 15

Met Ala Asp Val Ala Gly Thr Ser Asn Arg Asp Phe Arg Gly Arg Glu
1               5                   10                  15

Gln Arg Leu Phe Asn Ser Glu Gln Tyr Asn Tyr Asn Asn Ser Leu Asn
            20                  25                  30

Gly Glu Val Ser Val Trp Val Tyr Ala Tyr Tyr Ser Asp Gly Ser Val
        35                  40                  45

Leu Val Ile Asn Lys Asn Ser Gln Tyr Lys Val Gly Ile Ser Glu Thr
    50                  55                  60
```

-continued

```
Phe Lys Ala Leu Lys Glu Tyr Arg Glu Gly Gln His Asn Asp Ser Tyr
65                  70                  75                  80

Asp Glu Tyr Glu Val Asn Gln Ser Ile Tyr Tyr Pro Asn Gly Gly Asp
                85                  90                  95

Ala Arg Phe His Ser Asn Ala Lys Pro Arg Ala Ile Gln Ile Ile Phe
            100                 105                 110

Ser Pro Ser Val Asn Val Arg Thr Ile Lys Met Ala Lys Gly Asn Ala
        115                 120                 125

Val Ser Val Pro Asp Glu Tyr Leu Gln Arg Ser His Pro Trp Glu Ala
    130                 135                 140

Thr Gly Ile Lys Tyr Arg Lys Ile Lys Arg Asp Gly Glu Ile Val Gly
145                 150                 155                 160

Tyr Ser His Tyr Phe Glu Leu Pro His Glu Tyr Asn Ser Ile Ser Leu
                165                 170                 175

Ala Val Ser Gly Val His Lys Asn Pro Ser Ser Tyr Asn Val Gly Ser
            180                 185                 190

Ala His Asn Val Met Asp Val Phe Gln Ser Cys Asp Ser Ala Leu Arg
        195                 200                 205

Phe Cys Asn Arg Tyr Trp Ala Glu Leu Glu Leu Val Asn His Tyr Ile
    210                 215                 220

Ser Pro Asn Ala Tyr Pro Tyr Leu Tyr Ile Asn Asn His Ser Tyr Gly
225                 230                 235                 240

Val Ala Leu Ser Asn Arg Gln Arg Leu Leu Val
                245                 250


<210> SEQ ID NO 16
<211> LENGTH: 759
<212> TYPE: DNA
<213> ORGANISM: Bombyx mori

<400> SEQUENCE: 16

atggcagacg tagcaggaac aagtaaccga gactttcgcg gacgcgaaca aagactattc      60

aatagcgaac aatacaacta taacaacagc ttgaacggag aagtgagcgt gtgggtatac     120

gcatattact cagacgggtc tgtactcgta atcaacaaga actcgcaata caaggttggc     180

atttcagaga cattcaaggc acttaaggaa tatcgcgagg gacaacacaa cgactcttac     240

gatgagtatg aagtgaatca gagcatctac tatcctaacg gcggtgacgc tcgcaaattc     300

cactcaaatg ctaaaccacg cgcgatccag atcatcttca gtcctagtgt gaatgtgcgt     360

actatcaaga tggccaaagg taacgcggta tccgtgcccg atgagtacct acagcgatct     420

cacccatggg aagcgaccgg aatcaagtac cgcaagatta agagagacgg ggaaatcgtt     480

ggttacagcc attacttcga actaccccac gaatacaact ccatctccct agcggtaagt     540

ggtgtacata agaacccatc atcatacaat gtcggatcag cacataacgt aatggacgtc     600

ttccaatcat gcgactcggc tctcagattc tgcaaccgct actgggccga actcgaattg     660

gtgaaccact acatttcgcc gaacgcctac ccatacctct atatcaacaa tcatagctat     720

ggagtagctc tgagtaaccg tcagcgattg ctcgtgtaa                            759
```

DELIVERY METHOD

PRIORITY CLAIM TO RELATED APPLICATIONS

This application is a U.S. national stage filing under 35 U.S.C. § 371 from International Application No. PCT/GB2018/000064, filed on 11 Apr. 2018, and published as WO2018/189501 on 18 Oct. 2018, which claims the benefit under 35 U.S.C. 119 to United Kingdom Application No. GB 1705955.1, filed on 13 Apr. 2017, the benefit of priority of each of which is claimed herein, and which applications and publication are hereby incorporated herein by reference in their entirety.

FIELD OF THE INVENTION

This invention relates to a method of culturing cells.

BACKGROUND

The development and maintenance of the organisms requires many complex interactions between cells and extracellular matrix (ECM) components. Control of the cellular microenvironment is also important for assuring functionality of tissue engineered organ substitutes. The use of ECM mimics, which utilize collagen gel compaction, electromagnetic fields, electrospinning of nanofibers, mechanical stimulation and microstructured culture plates for artificial guidance of cells, have all been explored.

SUMMARY

The inventors have found that a polyhedron-based delivery system which releases growth factor (Polyhedra Delivery System, PODS) provides a stable physiologically relevant gradient of growth factor. The inventors' work investigates the activity of a growth factor gradient generated by a PODS which is set up by sustained release over a period of time, and is able to direct changes in relevant growth factor sensitive cells. The inventors have surprisingly found that using a PODS in this way allows differentiated cells with desired properties, such as directional growth, to be produced in the absence of extracellular matrix (ECM). Part of their work concerns preparation of an unbranched chain of neurons connected by axons.

Accordingly a first aspect of the invention provides a method of altering cells comprising culturing them in a growth factor gradient, wherein said gradient is provided by a polyhedra delivery system (PODS) that releases the growth factor to set up the gradient.

A second aspect of the present invention provides PODS as a therapeutic agent for use in a method of therapy.

A third aspect of the invention provides cells altered by the methods of the invention, optionally with a delivery vehicle, for use in a method of therapy.

DETAILED DESCRIPTION OF THE INVENTION

Terminology

Figure 1:
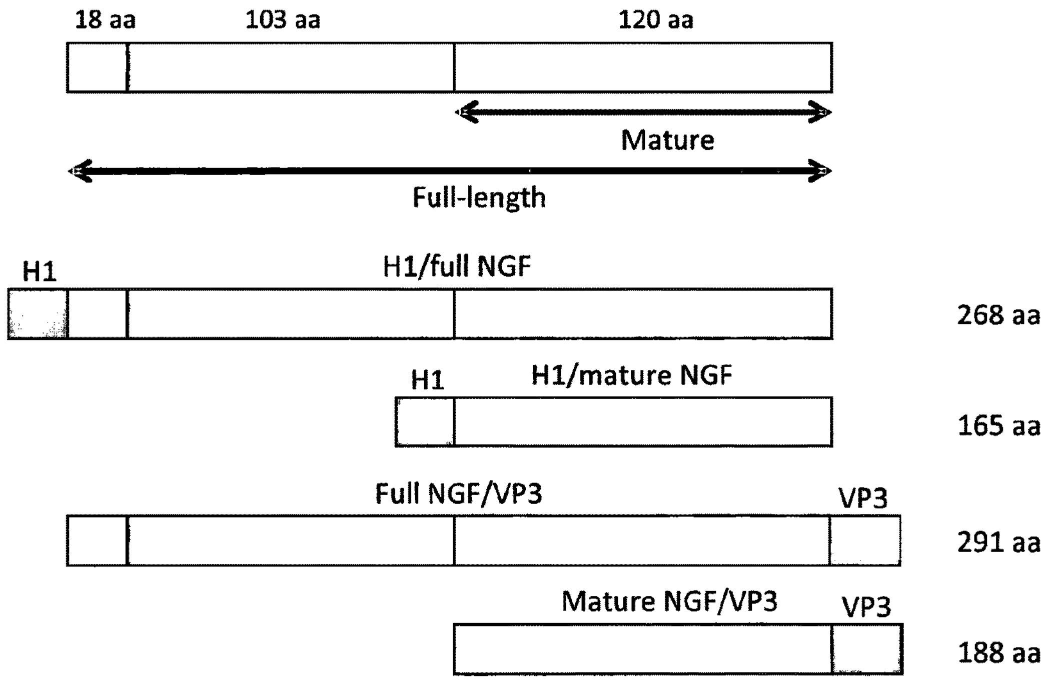
FIG. 1. Construction of NGF Polyhedra. Full length and mature NGF (full NGF and mature NGF, respectively) were fused with either a H1 or VP3 tag, and each recombinant NGF fusion protein was encapsulated into polyhedra.

The terms 'PODS', 'microcrystal' and 'crystal' are used interchangeably herein. However it should be understood that in embodiments which refer to 'microcrystal' or 'crystal' non-crystalline forms of PODS can also be used.

Characteristics of the Invention

When used in culture systems growth factors can be rapidly and homogenously diffused, but the imbalance and asymmetry of growth factors is important for the development of certain cells. The invention shows these complex phenomena can be reproduced in vitro by a PODS that releases a growth factor. The invention concerns altering cells by means of a gradient of growth factor generated by a PODS. The altering of the cells which occurs in the method of the invention may be due to one part of the cell being in contact with the growth factor at a different concentration from another part of the cell. It may be due to one cell being in communication or contact with another cell in contact with the growth factor at a different concentration. Through this mechanism the gradient is able to impart certain characteristic to the cell which would not be possible where the growth factor was present at a homogenous concentration, for example at the same concentration at each point of the cell surface. Further the fact that the gradient is unchanging is also an important in imparting the desired characteristic to the cell.

Culturing

The invention concerns culturing cells, which typically comprises placing them in conditions where they grow and/or differentiate. The conditions may be in vivo or in vitro, such as in a human or animal body.

Whilst the features of the invention will be described with reference to its in vitro embodiments these features may also apply to the in vivo embodiments as appropriate.

Culturing in vitro is typically in an aqueous medium. Optionally the culturing takes place in a medium comprising aqueous gel. The culturing may take place in a vessel, optionally a dish. The culturing may or may not take place on a coverslip, optionally in a culture medium in contact with a coverslip.

The culturing may be in any suitable system, for example a 2-dimensional or 3-dimensional system. The culturing may in static conditions, for example in which there is no flow of medium and/or there is no change in medium. In preferred embodiments medium is not changed for at least 10 hours, for example for at least 20, 30, 50, 100 or 500 hours.

The culturing will preferably take place in a medium in which is able to sustain the cells and/or allow them to grow. The medium typically comprises one or more nutrients. The medium may or may not be serum-free. The medium may comprise DMEM or neurobasal.

Cells

As used herein the term cells typically refers to eukaryotic cells, preferably human or animal cells, such as mammalian or avian cells. Optionally the cells described herein are neuronal cells. Preferably the cells are PC12 cells. Before culturing according to the methods of the invention the cells are typically undifferentiated cell such as stem cells or pluripotent precursor cells. The cells are typically non-specialized cells, or cells that are not mature, or cells that can undergo further stages in development. The shape of the cells before culturing is typically amorphous or spherical. The arrangement of the cells before culturing is typically incoherent, or without a well-defined order. The cells which are cultured may be continuous cell lines (e.g. with an immortal phenotype), primary cell cultures, transformed cell lines, finite cell lines (e.g. non-transformed cells), or any other cell population maintained in vitro. The cells may be isolated, purified or partially purified cells.

Neurons are preferred cells, and the method of the invention may result in formation of sympathetic neurons.

The cells are typically responsive to the growth factor. They may be of the same species as the growth factor. They may be cells associated with any condition mentioned herein and/or they may be cells which can be used to treat any condition mentioned herein. Whenever 'treatment' or 'treating' is mentioned it includes 'preventative' or 'prophylactic' uses. The cells may be associated with or responsible for any of the activities mentioned in herein or in Table 1.

Growth Factor

As used herein a growth factor is typically an extracellular protein capable of stimulating or inhibiting cellular growth, proliferation and cellular differentiation. Thus the growth factor may be a hormone or cytokine. The growth factor may be a natural or artificial one, and may for example be a homologue and/or fragment of a natural growth factor which retains growth factor activity. It may be a homologue and/or fragment of any specific growth factor mentioned herein, for example in Table 1. It may be a eukaryotic, preferably human or animal, such as mammalian or avian, growth factor.

The growth factor can be a neurotrophin. The expression 'Neurotrophin' is used interchangeably herein with the expression 'Neurotrophic growth factor'. Neurotrophins are the family of biomolecules that support the growth, survival and differentiation of both developing and mature neurons. The growth factor can be one or more members of one of the three main families, such as neurotrophin family (for example, nerve growth factor NGF, neurotrophin-3 NT-3, brain-derived neurotrophic factor BDNF, neurotrophin 4 NT-4 (also known as NT-5), ciliary neurotrophic factor (CNTF) family (CNTF, Leukemia inhibitory factor LIF, Interleukin-6), and GDNF (Glial cell-line neurotrophic factor) family (for example GDNF, CDNF, Artemin, Neuturin, Persephin). The growth factor may be a semaphorin or slit molecule.

Neurons can be cultured using gradients of neurotrophic growth factors. Nerve growth factor (NGF) can promote myelination and/or differentiation of neurons and/or axon growth and/or dendrite formation and/or elongation of the neuron perpendicular to the direction of the gradient and/or intermediate filament growth and/or tau protein expression and/or microtubule growth.

The growth factor can be a bone growth factor. A bone growth factor is a growth factor that stimulates the growth of bone tissue. Bone growth factors include bone morphogenetic proteins (BMPs), insulin-like growth factor (IGF-1), insulin-like growth factor-2 (IGF-2), transforming growth factor beta (TGF-b), fibroblast growth factors (FGFs), platelet-derived growth factor (PDGF), parathyroid hormone-related peptide (PTHrP), bone morphogenetic proteins (BMPs), and certain members of the growth differentiation factor (GDF) group of proteins. Preferred GDF proteins include:

GDF1—Studies in rodents suggest that this protein is involved in the establishment of left-right asymmetry in early embryogenesis and in neural development in later embryogenesis.

GDF2—This protein regulates cartilage and bone development, angiogenesis and differentiation of cholinergic central nervous system neurons.

GDF5—This protein regulates the development of numerous tissue and cell types, including cartilage, joints, brown fat, teeth, and the growth of neuronal axons and dendrites GDF7—This protein may play a role in the differentiation of tendon cells and spinal cord interneurons.

GDF10—This promotes neural repair after stroke.

GDF11—This protein plays a role in the development of the nervous and other organ systems, and may regulate aging.

The growth factor is preferably one which exerts an effect via microtubules, and or intermediate filaments/and or microfilaments, such as neuronal growth factors, or neurotrophins, for example NGF.

Table 1 describes preferred growth factors and exemplified constructs for expressing them, one or more of which may be used in the methods of the invention.

The growth factor in the gradient will be in purified or substantially purified form.

TABLE 1

| | GF PODS construct | Tag | Growth factor | Roles include: |
|---|---|---|---|---|
| 1 | Activin A-H1 H29S ΔCC | H1 | Activin | Cell proliferation, differentiation, apoptosis, metabolism, homeostasis, immune response, wound repair and endocrine function |
| 2 | BDNF-H1 H29S ΔCC | H1 | Brain-derived neurotrophic factor | Growth and differentiation of new neurons and synapses |
| 3 | BMP2-Full-H1 H29S ΔCC | H1 | Bone morphogenetic protein 2 | Stimulates production of bone |
| 4 | BMP-4-Full-H1 H29S ΔCC | H1 | Bone morphogenetic protein 4 | Differentiation in embryo, bone formation |

TABLE 1-continued

| | GF PODS construct | Tag | Growth factor | Roles include: |
|---|---|---|---|---|
| 5 | EGF-H1 H29S ΔCC | H1 | Epidermal growth factor | Cellular proliferation, differentiation, and survival |
| 6 | Endostatin B2-H1 H29S ΔCC | H1 | Endostatin | Blocks the proliferation and organization of endothelial cells into new blood vessels. Inhibits angiogenesis and growth of both primary tumours and secondary metastasis. |
| 7 | FGF2-H1 H29S ΔCC | H1 | Basic fibroblast growth factor | FGF family members bind heparin and possess broad mitogenic and angiogenic activities. FGF-2 causes limb and nervous system development, wound healing, and tumour growth. |
| 8 | FGF7-H1 H29S ΔCC | H1 | Keratinocyte growth factor | A potent epithelial cell-specific growth factor, whose mitogenic activity is predominantly exhibited in keratinocytes but not in fibroblasts and endothelial cells. Role in morphogenesis of epithelium, reepithelialization of wounds, hair development and early lung organogenesis. |
| 9 | GDNF-H1 H29S ΔCC | H1 | Glial Cell Derived Neurotrophic Factor | Promotes the survival and differentiation of dopaminergic neurons in culture, and prevents apoptosis of motor neurons induced by axotomy. |
| 10 | IGF-1-H1 H29S ΔCC | H1 | Insulin-like growth factor 1 | Primarily made by the liver as an endocrine hormone as well as in target tissues in a paracrine/autocrine fashion; produced throughout life. The highest rates of IGF-1 production occur during the pubertal growth spurt. The lowest levels occur in infancy and old age. |
| 11 | IL10-H1 H29S ΔCC | H1 | Interleukin 10 | This cytokine has pleiotropic effects in immunoregulation and inflammation. It down-regulates the expression of Th1 cytokines, MHC class II Ags, and costimulatory molecules on macrophages. It also enhances B cell survival, proliferation, and antibody production. |
| 12 | IL6-H1 H29S ΔCC | H1 | Interleukin 6 | Functions in inflammation and the maturation of B cells |
| 13 | LIF-H1 H29S ΔCC | H1 | Leukaemia Inhibitory Factor | Involved in the induction of hematopoietic differentiation in normal and myeloid leukemia cells, induction of neuronal cell differentiation, regulator of mesenchymal to epithelial conversion during kidney development |
| 14 | mEphrin B2-H1 H29S ΔCC | H1 | Ephrin B2 (species: mouse) | Implicated in mediating developmental events, especially in the nervous system and in erythropoiesis. |
| 15 | NGF-Full-H1 H29S | H1 | Nerve Growth Factor | NGF is a neurotrophic factor and neuropeptide primarily involved in the regulation of growth, maintenance, proliferation, and survival of certain target neurons. In fact, NGF is critical for the survival and maintenance of sympathetic and sensory neurons, as they undergo apoptosis in its absence. |
| 16 | NGF-Mature-H1 H29S ΔCC | H1 | | |
| 17 | PDGF-B-H1 H29S ΔCC | H1 | Platelet Derived Growth Factor | PDGF subunit B, which can homodimerize, bind and activate PDGF receptor tyrosine kinases, which play a role in a wide range of developmental processes. |
| 18 | Rank-L-H1 H29S ΔCC | H1 | Receptor activator of nuclear factor kappa-B ligand | RANK Ligand plays a critical role in bone metabolism, particularly osteoclast differentiation. In addition, RANK Ligand is expressed by some T cells and promotes dendritic cell maturation. Recombinant soluble human RANK Ligand is a non-glycosylated protein. |
| 19 | Rank-L-VP3 H29S ΔCC | VP3 | | |
| 20 | SCF-H1 H29S ΔCC | H1 | Stem Cell Factor; KIT Ligand | Cytokine that binds to the c-KIT receptor. SCF can exist both as a transmembrane protein and a soluble protein. This cytokine plays an important role in hematopoiesis (formation of blood cells), spermatogenesis, and melanogenesis. |
| 21 | SHH-H1 H29S ΔCC | H1 | Sonic Hedge Hog | Member of a small group of secreted proteins that are essential for development in both vertebrates and invertebrates. |
| 22 | TGFb1-H1 H29S ΔCC | H1 | Transforming Growth Factor Beta 1 | The protein regulates cell proliferation, differentiation and growth, and can modulate expression and activation of other growth factors including interferon gamma and tumor necrosis factor alpha. This gene is frequently upregulated in tumor cells. |

TABLE 1-continued

| | GF PODS construct | Tag | Growth factor | Roles include: |
|---|---|---|---|---|
| 23 | TGFb3-H1 H29S ΔCC | H1 | Transforming Growth Factor Beta 3 | The protein is involved in embryogenesis and cell differentiation, and plays a role in wound healing. |
| 24 | mVEGF-164-H1 H29S ΔCC | H1 | Vascular Endothelial Growth Factor (e.g. in the construct 164 amino acid variant, species mouse) | The protein induces proliferation and migration of vascular endothelial cells, and is essential for both physiological and pathological angiogenesis. |
| 25 | Wnt3a-H1 H29S ΔCC | H1 | Wingless-related integration site family, member3a | A role in oncogenesis and in several developmental processes, including regulation of cell fate and patterning during embryogenesis. |

Differentiation and/or Proliferation

Differentiation is typically the process whereby cells become specialized in order to perform a specific function. Through culturing according to the method of the invention cells can alter by acquiring specialized structural and/or functional features.

Proliferation is typically a process that results in an increase in the number of cells. Proliferation can be regulated by the slope (change in concentration per unit distance) of a gradient and/or by the direction of gradient.

Changes that Typically Occur in the Method of the Invention

The cells may alter in one or more structural features including:

Change of type: Cells can change to a different type in response to a gradient of growth factor. Cells can become a first type at one part of the gradient. Cells can become a second type at a second part of the gradient. For example for Wnt in mammals at the highest concentration establishes the posterior region whilst in areas of lowest concentration establishes the anterior region.

Change in arrangement or long range order: The cells can become more or less prevalent at one part of the gradient in comparison to uncultured cells or cultured cells grown in an equivalent uniform concentration of growth factor. The cells can become more or less prevalent at one part of the gradient in comparison to cells grown at a second part of the gradient. In one embodiment the cells are completely absent from certain points of the gradient. The cells or prominent cellular features, for example projections, such as neurites, optionally in axons or dendrites, can align in a direction which is well defined with respect to the direction of the gradient, for example along the gradient, or perpendicular to the gradient.

In one embodiment the cells align and/or attach to other (for example as described in the Examples). Such cells may align at a distance of 50 to 150 microns from the PODS, such as at a distance of 80 to 120 microns. In one embodiment there may be only a single set of aligned and/or attached cells (for example forming a circle), or there may be no aligned and/or attached cells outside the above distance ranges. The alignment is preferably autonomous, in that the gradient is the only cause of the alignment.

Change of shape: Cells can change shape optionally becoming elongated in shape, or can alter so that there is an increase in the cell surface to volume ratio. In an elongated cell the ratio of longest to shortest dimension is typically at least 2 to 1, at least 5 to 1, at least 10 to 1, at least 20 to 1, at least 100 to 1, at least 500 to 1, and optionally less than 100,000 to 1 or less than 10,000 to 1.

Change in expression profile: Cells can upregulate expression of proteins not expressed or minimally expressed compared to uncultured cells or cultured cells grown in equivalent uniform concentration of growth factor. Cells can downregulate expression of proteins not expressed or minimally expressed compared to uncultured cells or cultured cells grown in equivalent uniform concentration of growth factor. Cells can upregulate expression of one or more proteins and downregulate expression of one or more different proteins not expressed or minimally expressed compared to uncultured cells or cultured cells grown in equivalent uniform concentration of growth factor. Expression of proteins relevant to the structure of the cells may be upregulated, optionally proteins in filaments such as microfilaments, neurofilaments, microtubules, associated with microtubules such as tau. Expression of receptors can be upregulated. In one embodiment specific markers are expressed when the cells are altered.

Change in physical features: A change in the microtubules and/or microtubule associated proteins and/or intermediate filaments, for example tau and neurofilaments can occur, such as alignment of the microtubules or intermediate filaments, optionally neurofilaments, with respect to the gradient of growth factor, for example alignment of the longest dimension of the cell along the gradient of the growth factor or alignment of the shortest dimension of the cell along the gradient of the growth factor.

Cells cultured according to the methods of the invention may form lines (e.g. straight, curved or circular lines) of connecting cells, optionally where the line of cells is orientated perpendicular to the direction of the growth factor gradient.

Nerve cells, or neurons, cultured according to the method of the invention are preferably elongated in shape, and/or unbranched and/or have neurite projections at polar positions. Nerve cells may have axons and/or a growth cone/and or dendrites.

The Gradient

In the method of the invention the growth factor is not present at a homogenous concentration. Instead it is in the form of a gradient. As used herein, the gradient is typically the change in the value of growth factor concentration per unit distance in a particular direction, normally determined by sustained release by the PODS and diffusion through the medium. The concentration is preferably highest at the PODS and decreases with distance away from the PODS. The direction of the gradient is from the/a region containing PODS towards the/a region containing no PODS. For a circular arrangement of PODS in 2D or 3D the direction of the gradient is radially outwards from the PODS. For a linear arrangement of PODS the direction of the gradient is perpendicular to the axis along which the PODS are arranged. The gradient is provided by the PODS which, for example, break down and release growth factor in situ.

Growth factor is typically slowly released from the microcrystals field (which is the location where the PODS are), preferably resulting in a steady physiologically relevant gradient in growth factor at the periphery of the field. This microenvironment can result in the alteration of the cells in one or more ways as described in the paragraphs above. Typically for neurons, culturing in a growth factor gradient results in alteration of the cells in all of the ways described in the paragraphs above. The altering for neurons cultured in a growth factor gradient includes induction of differentiation and can induce alignment of cells, for example nerve cells, preferably PC12 cells.

Gradients will normally occur when the PODS is confined to a small part of the culture space. An important property of a PODS is that it typically generates short gradients. Short gradients are important for reducing off-target effects caused by high concentrations of growth factor diffusing to the surrounding area, for example to neighbouring tissues in therapeutic use. The concentration of growth factor in the gradients described herein is typically at a maximum in the microcrystals field. The concentration reduces as the distance from the microcrystals field increases, typically dropping to half of the maximum value at up to 5 microns, up to 10 microns, or up to 30 microns, or up to 60 microns, or up to 100 microns, or up to 150 microns from the microcrystals field. The PODS usually provide a 'short range' gradient, and in certain situations problems can arise with long range gradients. In one embodiment the gradient has a maximum size of up to 300 microns, such as up to 200 microns.

The gradients of the invention will be established in up to a day. The gradient may persist/last for at least 12 hours, 1 day, 5 days, 14 days, 30 days or 90 days. In a preferred embodiment the gradient is unchanging, or substantially unchanging. For example the concentration of the growth factor does not decrease by more than 10% over 12 hours, over 1 day or over 2 days at 10 microns from the PODS.

Microcrystals

Viruses such as cypoviruses and baculoviruses produce microcrystals which are crystals of the protein polyhedrin, also known as polyhedra. The microcrystals of the invention, or polyhedra, are typically regular arrays of the polyhedrin protein assembled in a cubic crystal lattice. The microcrystals are typically cubic in shape, or optionally form as irregular crystals. The microcrystals of the invention are typically isolated from cells, such as insect cells, which have been infected with virus, preferably baculovirus. The microcrystals typically range in size from 0.1 to 10 micron, for example 2 to 5 micron (measured as the maximum distance inside the microcrystal between different surfaces or the maximum length of an edge). The microcrystals typically comprise, for example encapsulate, one or more types of growth factor.

PODS and Polyhedra

The PODS used in the invention is typically in the form of, or comprises, microcrystals which comprise a structural protein and a growth factor. Each microcrystal (PODS) comprises more than one copy of the structural protein and growth factor, and typically comprises $10^7$ to $10^9$, for example $10^8$ polyhedron proteins and/or $10^7$ to $10^9$, for example $10^8$ growth factor molecules. Typically each PODS comprises $5\times10^7$ to $5\times10^8$ polyhedron proteins and/or $5\times10^7$ to $5\times10^8$ growth factor molecules.

The structural protein is typically capable of forming polyhedra, and is preferably a natural or artificial polyhedrin protein. The polyhedrin protein is typically of viral origin, for example a virus of the genus Cypovirus (CPV) or Baculovirus, such as a *Bombyx mori* cypovirus polyhedrin. Polyhedra are typically in the form of microcrystals which are preferably cubic crystals. Optionally PODS used in the methods of the invention have a maximum dimension (defined by distance between surfaces or length of an edge) of 1 micron, 2 micron, 1-4 micron, up to 10 micron, up to 15 micron or up to 20 micron. The polyhedrin protein typically has homology to all or a part of any such protein described herein.

Characteristics of the Crystal

Typically a crystal unit cell has a dimension of 100 angstroms, i.e. $1\times10^{-8}$ m. In a 1 micron crystal, a cube with each edge $10^{-6}$ m long, there are 100 unit cells along each edge, and so a 1 micron crystal has $100\times100\times100$ unit cells, i.e. $10^6$ unit cells. Each unit cell typically contains 24 copies of polyhedrin, so a 1 μm crystal has $24\times10^6$, or $2.4\times10^7$ copies of polyhedron, a density of $2.4\times10^7$ per $\mu m^3$. That means a 2 μm crystal has $2\times2\times2\times2.4\times10^7=19.2\times10^7$=approx. $2\times10^8$ copies of polyhedrin.

H1 tag: this replaces H1 in the polyhedrin. Assuming a 1 in 4 incorporation to minimise disrupting the crystal (H1 forms bunches of four), this would give 6 copies of H1-Growth factor per micron crystal, $6\times10^6$ per $\mu m^3$, and so typically so a 1 $\mu m^3$ sized PODS contains $6\times10^6$ per $\mu m^3$ copies of growth factor.

VP3 tag: potentially 1 VP3 binding site per polyhedrin molecule, so up to $2.4\times10^7$ per $\mu m^3$, and $2.4\times10^7$ copies in a 1 μm crystal.

Typically a crystal comprises $10^7$ to $10^9$ molecules of growth factor, such as about $10^8$ molecules.

Attaching, Encapsulating or Packaging Growth Factor

The PODS of the invention comprises growth factor. This is typically immobilised and/or attached to the PODS in manner that allows release to provide the gradient. In a preferred embodiment the growth factor comprises a tag that is used to attach it to the PODS.

The growth factor can be targeted for packaging in a polyhedra by attachment of the tag to the growth factor. The growth factor polypeptide can typically comprise the growth factor amino acid sequence and the amino acid sequence of part of the polyhedrin protein, preferably helix 1 (H1), even more preferably a sequence with at least 80% homology to an H1 sequence mentioned herein. The growth factor polypeptide can comprise the growth factor amino acid sequence and the amino acid sequence of part of the baculovirus coat protein, preferably VP3, even more preferably a sequence with at least 80% homology to a VP3 sequence disclosed herein. A short VP3 sequence is preferred to minimise any disruptive effect on the PODS.

PODS incorporating growth factor can be prepared by coexpressing polyhedrin protein and polypeptide comprising a targeting portion and a growth factor portion. Cells can be inoculated with recombinant baculovirus expressing polyhedrin to generate empty polyhedra. Cells can be coinfected with recombinant baculovirus expressing polyhedrin and recombinant baculovirus expressing a polypeptide comprising the growth factor and a tag which targets the growth factor for packaging, for example VP3 or H1. PODS comprising polyhedrin and the polypeptide can be prepared. Cells can be coinfected with recombinant baculovirus expressing polyhedrin and one or more different recombinant baculoviruses each expressing a different polypeptide comprising the growth factor and a tag which targets the growth factor for packaging.

PODS comprising polyhedrin and one or more different polypeptides, encoding one or more different growth factors, can be prepared. The different polypeptides can have the same tag or different tags.

The polyhedrin protein can be *Bombyx mori* cypovirus polyhedrin protein. The recombinant baculovirus can be AcCP-H29 expressing *Bombyx mori* cypovirus polyhedrin. The cells used to produce the PODS, or growth factor-encapsulated polyhedral, can be *Spodoptera frugiperda* IPLB-SF21-AE cells (Sf cells). The PODS can be isolated from the cells, optionally insect cells, by centrifugation.

The PODS can be prepared in an aqueous suspension. The concentration of the PODS suspension can be more than $10^4$ PODS per microliter volume, typically from $10^4$ to $10^7$ PODS per microliter volume, preferably from $5\times10^4$ to $5\times10^6$ or $10^5$ to $10^6$ PODS per microliter volume. PODS can be applied to (contacted with) the culture system/medium at these concentrations. These can be used in therapy at concentrations of $10^5$ to $10^7$ crystals per microliter, for example at $3\times10^6$ crystals per microliter.

The Microcrystals (PODS) Field

The microcrystals field is the location of the microcrystals (that set up the gradient). The term 'microcrystals field' includes the feature of a 'PODS field' where the PODS are not in crystalline form.

The geometry and size of the microcrystals field may depend on the growth factors. The microcrystals field can be a circular, linear or rectangular field. The shape of the field can be customized for a particular use, for example it can be a curved, including S-shaped, or it can be a shape consisting of straight lines, such as a square, hexagon or an octagon. The microcrystals field can comprise $10^4$-$10^8$, preferably $10^5$-$10^7$ or $5\times10^5$-$10^6$ microcrystals in total, or this range of microcrystals in 20 $mm^2$. The field can comprise up to $10^5$ microcrystals, or up to $10^6$ microcrystals, for example in 20 $mm^2$. The microcrystals field can comprise one or more shape elements, for example one or more lines. Each shape element can comprise these stated ranges of microcrystals, for example $10^4$-$10^5$ microcrystals, or up to $10^5$ microcrystals, or up to $10^6$ microcrystals.

A microcrystals field can comprise one or more lines or shapes. The lines can be straight lines. The lines and/or shapes may be spaced so that the concentration of growth factor reaches substantially zero between the lines and/or shapes. Adjacent lines or shapes may each comprise the same growth factor. Adjacent lines or shapes may each comprise a different growth factor. The lines and/or shapes may intersect. For example, the lines may form a regular grid pattern. One or more lines or shapes may comprise one or more different growth factors. In a preferred embodiment the field is a 0.5 to 10 mm diameter, for example 1 to 8 or 2 to 4 mm diameter circular field.

A grid structure is envisaged in which individual lines of the grid can contain different growth factor combinations. Adjacent and intersecting grid lines can provide areas where complex gradients will develop, allowing the creation of a wide range of defined and addressable culture conditions in a small area. The lines of the grid can be placed up to 0.1 mm, up to 1 mm, up to 5 mm, from 0.1 mm to 1 mm, from 1 mm to 5 mm, apart.

In the methods herein, the microcrystals field may be applied to a surface, for example the surface of a coverslip, the surface of a cell culture vessel, or the surface of a delivery vehicle such as hydrogel. The microcrystals field may be applied by hand, for example using a micropipette, or may be applied using a robot or other methods of surface deposition including lithography. The microcrystals field can be dried after application to a surface, for example for more than 3 hours. The microcrystals field may be extruded into hydrogel for example using a syringe. The use of a hydrogel or other carrier can increase the duration of the gradient. Synthetic hydrogels or natural materials, preferably collagen, can be used as a delivery vehicle. A field of PODS as described herein can be provided in a delivery vehicle such as a layer of hydrogel which can be manipulated, for example to provide a gradient of growth factor in a defined direction along a pre-determined path. For example, in one embodiment the methods provide an insulated line of PODS spanning an injury to encourage axons to navigate across the injury.

For neuronal growth factors a linear pattern is envisaged. There are any number of different geometries that may be effective. One possibility is creating 3D sandwiches of cells and PODS. A microcrystal field comprising parallel lines of PODS (0.1 to 1 mm apart) can be created. A layer of soft hydrogel or other delivery system vehicle could be layered on this and optionally seeded with neuronal cells or neuronal precursor cells. A stiffer layer of hydrogel can be layered above. After the gel has set, the gel can be manipulated to change the 3D disposition of the lines of PODS. For example, the structure could be rolled to create a "Swiss roll" of cells and PODS. The nerve cells would form linear, unbranched connections perpendicular to the gradient, and therefore along the lines of PODS. This entire structure comprising PODS and cells could be used as an implant, for example to restore nerves that had been lost due to neurodegeneration or injury.

PODS are typically denser than water, and can sink to the bottom of aqueous cell culture medium in a few seconds to within 10 minutes. PODS may be held in place in a culture system by gravity. The microcrystals may be added to a drop of cell culture medium suspended from a surface, optionally example a plastic surface, for example a coverslip. This would establish a gradient across the drop with cells at the bottom experiencing the highest concentrations.

Any suitable may be used to place or attach the PODS. In one embodiment the PODS is attached via a micropatterning system, for example using a photoactivatable reagent and a UV illumination system.

Embodiments

In one embodiment the method of the invention does not comprise a component that mimics an extracellular matrix, for example it might not comprise collagen gel compaction, an electromagnetic field, electrospinning of cells, mechanical stimulation and microstructured culture plates.

For the avoidance of doubt any feature described herein, such as specific growth factors or specific properties of cells may be excluded in certain embodiments of the invention.

Medical Use

The invention includes setting up a gradient for use in therapy. Therefore the invention includes administering the PODS for preventing or treating a condition, such as any condition mentioned herein.

Preferred conditions include growth factor deficiency, degeneration, injury or nerve damage. The PODS may be used in the manufacture of a medicament for preventing or treating a condition. Thus the PODS may be used in therapy, optionally together with a delivery vehicle, for example collagen or a gel (such as a hydrogel). The PODS may be delivered using a scaffold. Examples of diseases that can be treated by the PODS are mentioned herein, including in Table 1.

In preferred embodiments:

PODS for therapy of ALS can comprise IGF-1.

PODS for therapy of Parkinson's can comprise GDNF, GDF-5, and/or CDNF.

PODS for cartilage repair can comprise the TGFb family.

PODS for therapy of multiple sclerosis can comprise LIF.

PODS for therapy of bone fracture can comprise bone morphogenetic protein 2 or bone morphogenetic protein 4

PODS for therapy of ALS or cardiac conditions can comprise VEGF.

Cells prepared using the method of the invention may be used in therapy, for example to treat any condition mentioned herein, such as degeneration, injury or nerve damage. In a preferred embodiment nerve cells prepared in a gradient of neurotrophic growth factors, can be used in a method of treatment for nerve injury or for neurodegeneration.

Homologues and Fragments

Homologues of polypeptide sequences are referred to herein (for example growth factors and tags). Such homologues typically have at least 70% homology, preferably at least 80%, at least 85%, at least 90%, at least 95%, at least 97%, at least 98% or at least 99% homology, for example over a region of at least 10, 15, 20, 30, 100 or more contiguous amino acids. The homology may be calculated on the basis of amino acid identity (sometimes referred to as "hard homology"). Preferred homologues retain activity, for example growth factor or tag activity.

The UWGCG Package provides the BESTFIT program which can be used to calculate homology and/or % sequence identity (for example used on its default settings) (Devereux et al (1984) Nucleic Acids Research 12, p 387-395). The PILEUP and BLAST algorithms can be used to calculate homology and/or % sequence identity and/or line up sequences, such as identifying equivalent or corresponding sequences (typically on their default settings), for example as described in Altschul S. F. (1993) J Mol Evol 36:290-300; Altschul, S, F et al (1990) J Mol Biol 215:403-10.

Software for performing BLAST analyses is publicly available through the National Center for Biotechnology Information. This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W5 T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89: 10915-10919) alignments (B) of 50, expectation (E) of 10, M=5, N=4, and a comparison of both sequences.

The BLAST algorithm performs a statistical analysis of the similarity between two sequences; see e.g., Karlin and Altschul (1993) Proc. Natl. Acad. Sci. USA 90: 5873-5787. One measure of similarity provided by the BLAST algorithm is the smallest sum probability (P(N)), which provides an indication of the probability by which a match between two polynucleotide sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologous sequence typically differs by 1, 2, 3, 4 or more amino acids, such as less than 10, 15 or 20 amino acids (which may be substitutions, deletions or insertions of amino acids). These changes may be measured across any of the regions mentioned above in relation to calculating homology and/or % sequence identity.

Fragments of any of the polypeptides mentioned herein can be used. Typically such fragments retain the original activity, for example growth factor or tag activity. The fragments typically comprise at least 60%, for example at least 70%, 80%, 90% or 95% of the original sequence.

Therapeutic Agents

Therapeutic agents (PODS and cells) and uses are mentioned herein. The invention provides such agents for use in preventing or treating the relevant condition. This may comprise administering to an individual in need a therapeutically effective amount of the agent. The invention provides use of the agent in the manufacture of a medicament to prevent or treat the disease.

The formulation of the agent will depend upon the nature of the agent. The agent will be provided in the form of a pharmaceutical composition containing the agent and a pharmaceutically acceptable carrier or diluent. Suitable carriers and diluents include isotonic saline solutions, for example phosphate-buffered saline. The agent may be formulated for parenteral, intravenous, intramuscular, subcutaneous, transdermal or oral administration. Preferably administration can be by injection, nasal (a spray or dry powder), by inhaler or as eye drops.

The dose of an agent may be determined according to various parameters, especially according to the substance used; the age, weight and condition of the individual to be treated; the route of administration; and the required regimen. A physician will be able to determine the required route of administration and dosage for any particular agent. A suitable dose may however be from 0.1 to 100 mg/kg body weight such as 1 to 40 mg/kg body weight, for example, to be taken from 1 to 3 times daily.

EXAMPLES

Example 1. Generic Method for Construction, Expression and Purification of Growth Factor Polyhedra of Table 1

The requisite cDNA for selected growth factors (see Table 1) was purchased from commercial suppliers. Using standard cloning techniques, growth factors sequences were cloned and subsequently subcloned into transfection the plasmids pDEST/VP3 and/or pDEST/H1), resulting in the production of transfer vectors encoding a growth factor sequence fused to VP3 or H1 tags, C-terminally or N-terminally, respectively. Then, *Spodoptera frugiperda* cells were co-transfected with growth factor transfection vectors and a linear version of non-recombinant parent baculovirus DNA. The successful homologues recombination within insect cells inserted growth factor sequences into the baculovirus genome and so created a recombinant baculovirus variant that allowed the co-expression of a tagged growth factor protein and the polyhedrin protein, both under the control of the polyhedrin promoter for maximum efficiency.

Recombinant baculovirus was amplified as required and growth factor polyhedra were subsequently expressed in suspension insect cell cultures using a shaking incubator for 7-10 days at 27° C. The rapid progress of the cubic growth factor polyhedra expression was monitored by microscope. After culturing for 7-10 days, polyhedra containing cells were harvested by centrifugation and cell pellets stored at −20° C.

Growth factor polyhedra were isolated from insect cells by cell lysis and next purified by at least 3 rounds of PBS washes (from commercial suppliers, pH 7.6-7.9), followed by centrifugation at 3000×g, 4° C., or until a pure product has been achieved, where pure polyhedrin is characterised by a milky-white appearance in aqueous liquid, depending on the concentration of polyhedra, and was readily assessed under a standard bright field microscope with a 20× and 40× magnification. Lastly, growth factor polyhedra were counted and stored at 4° C. in PBS (pH 7.6-7-9).

Example 2. Construction of NGF Polyhedra

The cDNA encoding the NGF ORF was purchased from Toyobo in an entry vector. The full-length (241 amino acids) and mature (120 amino acids) form NGF were cloned and subcloned into each destination vector (pDEST/VP3, and pDEST/H1), resulting in production of the transfer vectors encoding the full-length or mature form of NGF fused with VP3 or H1 tags (pTransH1/full NGF, pTransH1/mature NGF, pTransVP3/full NGF, and pTransVP3/mature NGF). These transfer vectors were co-transfected into Sf21 and/or Sf9 insect cells with BaculoGold™ baculovirus linearized DNA. After incubation for 5 days at 27° C., recombinant baculoviruses expressing the full-length and mature forms of NGF with VP3 or H1 tags were harvested and stored at 4° C.

Full-length or mature NGF was fused with polyhedron-targeting tags (H1 or VP3) to obtain NGF-encapsulated polyhedra (PODS NGF) (FIG. 1).

Example 3. Purification of NGF-Encapsulated Polyhedra

To generate empty polyhedra, *Spodoptera frugiperda* IPLB-5F21-AE cells (Sf cells) were inoculated with recombinant baculovirus AcCP-H29S expressing *Bombyx mori* cypovirus polyhedrin under the control of the baculovirus polyhedrin promoter. For production of NGF polyhedra (PODS NGF), Sf cells were co-infected with AcCP-H29S and another recombinant baculovirus expressing recombinant NGF fused with the VP3 or H1 tags. The infected cells were cultured for 10 days at 27° C. and then the cells were harvested in a conical tube by centrifugation. The cell pellet was resuspended in phosphate-buffered saline (PBS; pH 7.2) and treated with an ultrasonic homogenizer at 6% power for 30 sec. The cell homogenate was centrifuged at 1500×g at 4° C. and the supernatant was removed. These treatments were repeated and the purification was complete. The polyhedron suspension was adjusted to $5\times10^4$ or $1\times10^5$ numbers per microliter volume and stored at 4° C. in distilled water containing 100 units/ml penicillin and 100 μg/ml streptomycin.

Example 4. Methods for Preparing a Gradient a. Circular patch: Cover slip coating. Cover slips were sterilized with 70% ethanol and subsequently washed with sterilized water. Cellmatrix Type IV was dissolved in 0.15 M acetic acid (30 μg/mL). Sterilized cover slips were put and 0.5 mL of Cellmatrix Type IV solution was then added to culture wells. Following overnight incubation, the Cellmatrix Type IV solution was discarded and the cover slips were allowed to dry for 1 h. Collagen-coated cover slips were washed twice with serum-free DMEM. One microliter of polyhedron suspension ($5\times10^4$ or $1\times10^5$ numbers/μl) was spotted on the cover slips and allowed to dry for more than 3 h.

Example 5. Culturing NGF

One microliter of PODS NGF suspension ($5\times10^4$ or $1\times10^5$ crystals/μl) was manually spotted onto a gelatin-coated cover slip using a micropipette to create a circular field of approximately 2-4 mm in diameter of either PODS full-length NGF or PODS mature NGF (FIG. 1). PC12 cells were seeded and cultured with serum-free medium under static conditions for 96 hours without media change. At the end of this period, alignment of PC12 cells along the periphery of the PODS fields was observed. PODS full-length NGF prominently induced axon extension from each cell. This axon extension was parallel with the edge of the PODS field resulting in the formation of a connected chain of migrated cells.

Example 6. Observation of Cells by SEM Imaging

Alignment and axon extension of PC12 cells surrounding PODS NGF field was also observed by scanning electron microscopy (SEM).

PC12 Cell Culture.

The PC12 DMEM cell culture medium was discarded and 0.02% EDTA solution was added. After the EDTA solution was discarded, 1 ml of 0.25% trypsin-EDTA was added and incubated for 1 min. One millilitre of DMEM culture medium was added and the cell suspension was centrifuged at 1,200 rpm for 2 min. After the supernatant was discarded, cells were suspended in 1 ml of serum-free DMEM and the number of cells was counted. Cells ($7\times10^4$ cells/well) were then seeded into a well. Half of the medium (serum-free DMEM) was gently exchanged after 3 days. Images of cell alignment were obtained via scanning electron microscopy (SEM) on the 5th day following cell seeding.

Preparation of Cells for SEM Imaging.

After the cell medium was gently discarded, cells were fixed by 4% paraformaldehyde phosphate buffer solution, 1% osmium tetroxide and 1% tannic. Dehydration was carried out by immersing the cover slips in a series of ethanol solutions of increasing concentrations until 100% dehydration was achieved. Cover slips were covered with hexamethyldisilazane and allowed to dry overnight. Images of cell alignment were obtained via SEM after gold-sputtering (200 Å).

Immunocytochemistry.

For immunofluorescence, cells on the cover slips were fixed for 30 min at room temp with 4% paraformaldehyde. After three washes with PBS for 5 min each, the cells were permeabilized with 0.3% Triton X-100 in PBS for 15 min at room temperature. After three washes with PBS for 5 min each, the cells were incubated in blocking buffer (3% FBS in PBS) for 1 h at room temperature and then incubated with primary antibodies (anti-tau antibody (Merck Millipore) or anti-neurofilament heavy polypeptide antibody (SIGMA)) for overnight at 4° C. After three washes with PBS for 10 min each, the cells were incubated with FITC-conjugated secondary antibody (goat anti-mouse IgG antibody (Invitrogen)) for 1 h at room temperature. Cover slips were then washed three times with PBS and finally mounted on microscope slides in mounting medium with propidium Iodide (Invitrogen) for nuclei staining. Stained cells were observed using an Olympus Fluoview FV1000-IX81 confocal microscope.

Figure 2:
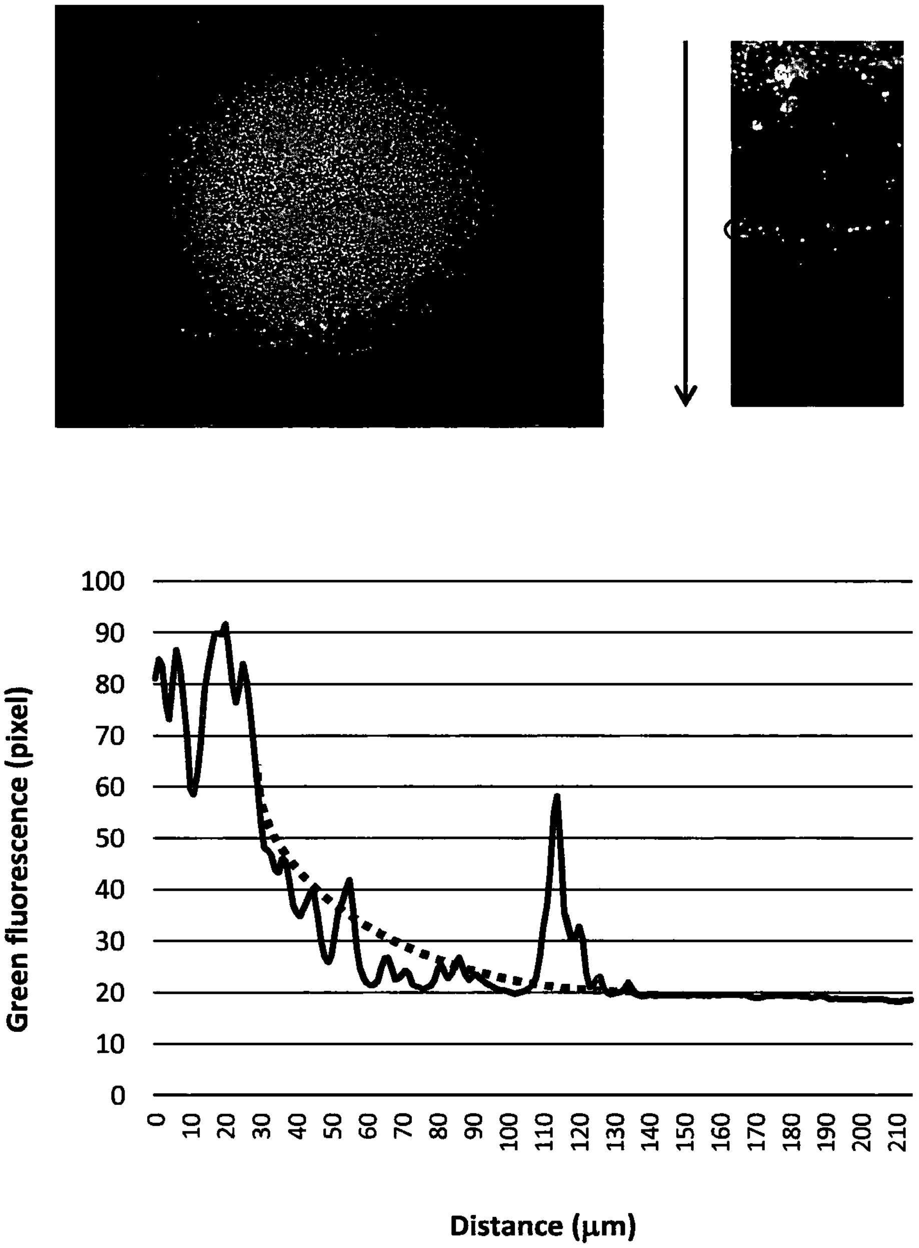
FIG. 2. PODS EGFP and PODS NGF were mixed and spotted. PC12 cells were seeded and incubated for 5 days (left). Green fluorescence was scanned within the white box (middle) and measured by counting the number of pixels that exhibited green fluorescence (right). The aligned PC12 cells were detected by the fluorescence from PODS field. The dotted line indicates the extent of the EGFP gradient FIG. 3. PC12 cells were incubated with PODS H1/full NGF. PC12 cells were incubated with PODS H1/full NGF. Expression of tau and neurofilament which was induced by PODS NGF was analyzed by immunofluorescence cytochemistry. Nuclei were stained with propidium iodide (PI). Connection of PC12 cells via the extended axon was observed. The extended axon which was induced by PODS NGF was detected by expression of neurofilament. The solid box shows the connection between the extended axon and the growth cone-like structure.

These results indicate that PODS NGF field regulates the direction of alignment and axon extension of PC12 cells. We confirmed the differentiation of PC12 cells using tau and neurofilament antibodies. Tau and neurofilament proteins were observed in the aligned PC12 cells (FIG. 2*a*). Neurofilament was notably detected extending from the extended axon, indicating that the aligned cells are differentiated to nerve cells. A helical structure of neurofilament was also observed in the neighborhood of the tip of the extended axons. In contrast, expression of tau and neurofilament was not observed in PC12 cells incubated with empty polyhedra. In some cases the connections of PC12 cells were seen to be formed between the extended axon and the growth cone-like structure which were induced by PODS H1/full NGF (a solid box in FIG. 2*b*), but in other cases the connection was not observed (a dotted box in FIG. 2*b*).

Example 7 Direct Visualisation of a Gradient

Figure 3:
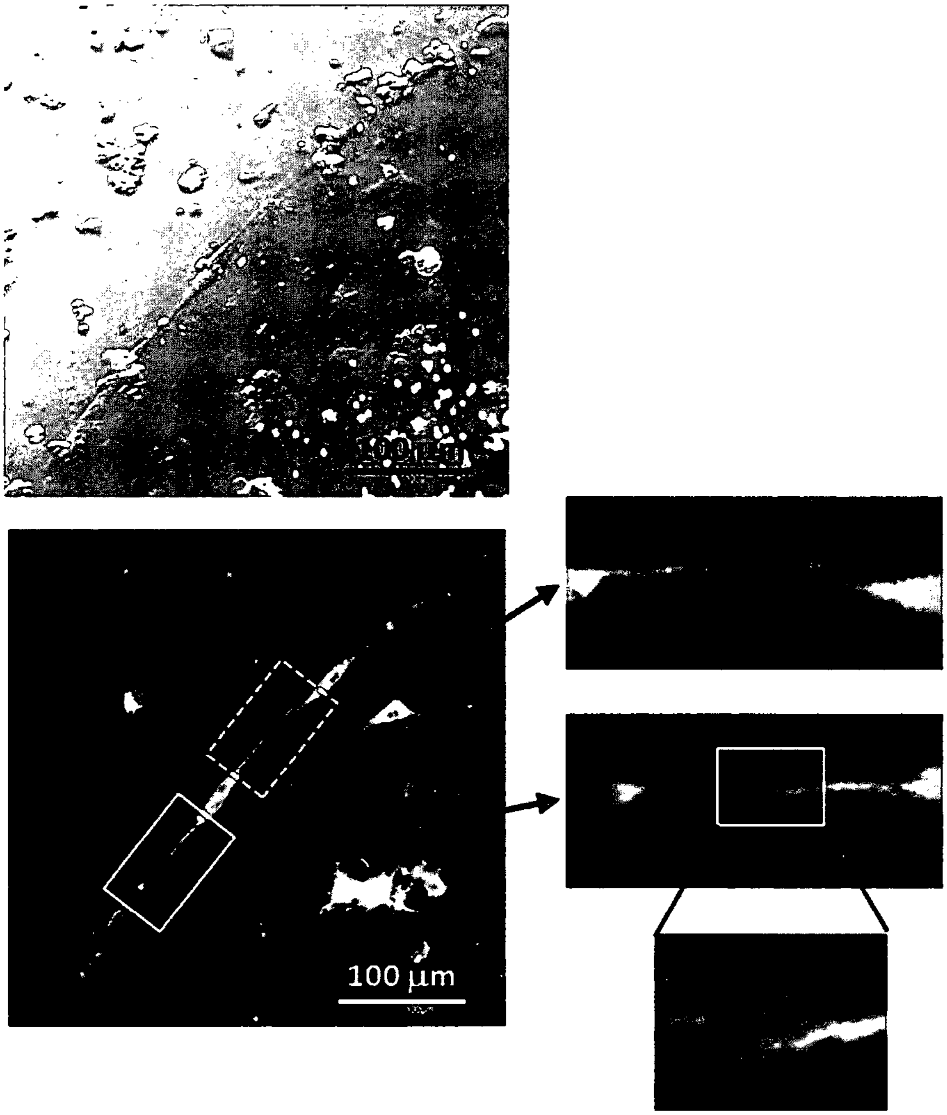

To determine the extent of the gradient, PODS NGF were mixed with polyhedra encapsulating enhanced green fluorescent protein (PODS EGFP), and subsequently spotted on a cover slip. PC12 cells were then seeded and incubated with PODS NGF and PODS EGFP, and the fluorescence emission on the periphery of the aligned PC12 cells was measured (FIG. 3). A gradient of green fluorescence was observed from the polyhedra field.

```
DNA and Protein Sequences
NGF (mature) sequence:
TCATCATCCCATCCCATCTTCCACAGGGGCGAATTCTCGGTGTGTGACAG

TGTCAGCGTGTGGGTTGGGGATAAGACCACCGCCACAGACATCAAGGGCA

AGGAGGTGATGGTGTTGGGAGAGGTGAACATTAACAACAGTGTATTCAAA

CAGTACTTTTTTGAGACCAAGTGCCGGGACCCAAATCCCGTTGACAGCGG

GTGCCGGGGCATTGACTCAAAGCACTGGAACTCATATTGTACCACGACTC

ACACCTTTGTCAAGGCGCTGACCATGGATGGCAAGCAGGCTGCCTGGCGG

TTTATCCGGATAGATACGGCCTGTGTGTGTGTGCTCAGCAGGAAGGCTGT

GAGAAGAGCCTGA

SSSHPIFHRGEFSVCDSVSVWVGDKTTATDIKGKEVMVLGEVNINNSVFK

QYFFETKCRDPNPVDSGCRGIDSKHWNSYCTTTHTFVKALTMDGKQAAWR

FIRIDTACVCVLSRKAVRRA*

H1-NGF fusion protein sequence
atggcagacgtagcaggaacaagtaaccgagactttcgcggacgcgaaca

aagactattcaatagcgaacaatacaactataacaAcagcAAGAATTCTA

GACCATCAACAAGTTTGTACAAAAAAGCAGGCTCCTCATCATCCCATCCC

ATCTTCCACAGGGGCGAATTCTCGGTGTGTGACAGTGTCAGCGTGTGGGT

TGGGGATAAGACCACCGCCACAGACATCAAGGGCAAGGAGGTGATGGTGT

TGGGAGAGGTGAACATTAACAACAGTGTATTCAAACAGTACTTTTTTGAG
```

-continued

```
ACCAAGTGCCGGGACCCAAATCCCGTTGACAGCGGGTGCCGGGGCATTGA

CTCAAAGCACTGGAACTCATATTGTACCACGACTCACACCTTTGTCAAGG

CGCTGACCATGGATGGCAAGCAGGCTGCCTGGCGGTTTATCCGGATAGAT

ACGGCCTGTGTGTGTGTGCTCAGCAGGAAGGCTGTGAGAAGAGCCTGA

MADVAGTSNRDFRGREQRLFNSEQYNYNNSKNSRPSTSLYKKAGSSSSHP

IFHRGEFSVCDSVSVWVGDKTTATDIKGKEVMVLGEVNINNSVFKQYFFE

TKCRDPNPVDSGCRGIDSKHWNSYCTTTHTFVKALTMDGKQAAWRFIRID

TACVCVLSRKAVRRA*

NGF-VP3 fusion protein sequence
ATGTCATCATCCCATCCCATCTTCCACAGGGGCGAATTCTCGGTGTGTGA

CAGTGTCAGCGTGTGGGTTGGGGATAAGACCACCGCCACAGACATCAAGG

GCAAGGAGGTGATGGTGTTGGGAGAGGTGAACATTAACAACAGTGTATTC

AAACAGTACTTTTTTGAGACCAAGTGCCGGGACCCAAATCCCGTTGACAG

CGGGTGCCGGGGCATTGACTCAAAGCACTGGAACTCATATTGTACCACGA

CTCACACCTTTGTCAAGGCGCTGACCATGGATGGCAAGCAGGCTGCCTGG

CGGTTTATCCGGATAGATACGGCCTGTGTGTGTGTGCTCAGCAGGAAGGC

TGTGAGAAGAGCCATGGGTCGAAAGAACATGTTTCACCATGATGGGTACC

TTCTAGCTTTCAACTCACAACGACGATCACACACGTTACGACTACTAGGG

CCTTTTCAGTACTTCAACTTCTCCGAGACAGATAGAGGACATCCATTATT

TCGCCTACCTCTTAAGTATCCATCAAAAGCAATACCAGCAGATGAGTTAA

TTGACAATTTACACTAGTAACGGCGGAATAA

MSSSHPIFHRGEFSVCDSVSVWVGDKTTATDIKGKEVMVLGEVNINNSVF

KQYFFETKCRDPNPVDSGCRGIDSKHWNSYCTTTHTFVKALTMDGKQAAW

RFIRIDTACVCVLSRKAVRRAMGRKNMFHHDGYLLAFNSQRRSHTLRLLG

PFQYFNFSETDRGHPLFRLPLKYPSKAIPADELIDNLH*

NGF (full length) sequence:
GAACCACACTCAGAGAGCAATGTCCCTGCAGGACACACCATCCCCCAAGT

CCACTGGACTAAACTTCAGCATTCCCTTGACACTGCCCTTCGCAGAGCCC

GCAGCGCCCCGGCAGCGGCGATAGCTGCACGCGTGGCGGGGCAGACCCGC

AACATTACTGTGGACCCCAGGCTGTTTAAAAAGCGGCGACTCCGTTCACC

CCGTGTGCTGTTTAGCACCCAGCCTCCCCGTGAAGCTGCAGACACTCAGG

ATCTGGACTTCGAGGTCGGTGGTGCTGCCCCCTTCAACAGGACTCACAGG

AGCAAGCGGTCATCATCCCATCCCATCTTCCACAGGGGCGAATTCTCGGT

GTGTGACAGTGTCAGCGTGTGGGTTGGGGATAAGACCACCGCCACAGACA

TCAAGGGCAAGGAGGTGATGGTGTTGGGAGAGGTGAACATTAACAACAGT

GTATTCAAACAGTACTTTTTTGAGACCAAGTGCCGGGACCCAAATCCCGT

TGACAGCGGGTGCCGGGGCATTGACTCAAAGCACTGGAACTCATATTGTA

CCACGACTCACACCTTTGTCAAGGCGCTGACCATGGATGGCAAGCAGGCT

GCCTGGCGGTTTATCCGGATAGATACGGCCTGTGTGTGTGTGCTCAGCAG

GAAGGCTGTGAGAAGAGCCTGA

EPHSESNVPAGHTIPQVHWTKLQHSLDTALRRARSAPAAAIAARVAGQTR

NITVDPRLFKKRRLRSPRVLFSTQPPREAADTQDLDFEVGGAAPFNRTHR
```

-continued

SKRSSSHPIFHRGEFSVCDSVSVWVGDKTTATDIKGKEVMVLGEVNINNS
VFKQYFFETKCRDPNPVDSGCRGIDSKHWNSYCTTTHTFVKALTMDGKQA
AWRFIRIDTACVCVLSRKAVRRA*

H1-NGF (full length) fusion protein sequence:
atggcagacgtagcaggaacaagtaaccgagactttcgcggacgcgaaca
aagactattcaatagcgaacaatacaactataacaAcagcAAGAATTCTA
GACCATCAACAAGTTTGTACAAAAAAGCAGGCTCCGAACCACACTCAGAG
AGCAATGTCCCTGCAGGACACACCATCCCCCAAGTCCACTGGACTAAACT
TCAGCATTCCCTTGACACTGCCCTTCGCAGAGCCCGCAGCGCCCCGGCAG
CGGCGATAGCTGCACGCGTGGCGGGGCAGACCCGCAACATTACTGTGGAC
CCCAGGCTGTTTAAAAAGCGGCGACTCCGTTCACCCCGTGTGCTGTTTAG
CACCCAGCCTCCCCGTGAAGCTGCAGACACTCAGGATCTGGACTTCGAGG
TCGGTGGTGCTGCCCCCTTCAACAGGACTCACAGGAGCAAGCGGTCATCA
TCCCATCCCATCTTCCACAGGGGCGAATTCTCGGTGTGTGACAGTGTCAG
CGTGTGGGTTGGGGATAAGACCACCGCCACAGACATCAAGGGCAAGGAGG
TGATGGTGTTGGGAGAGGTGAACATTAACAACAGTGTATTCAAACAGTAC
TTTTTTGAGACCAAGTGCCGGGACCCAAATCCCGTTGACAGCGGGTGCCG
GGGCATTGACTCAAAGCACTGGAACTCATATTGTACCACGACTCACACCT
TTGTCAAGGCGCTGACCATGGATGGCAAGCAGGCTGCCTGGCGGTTTATC
CGGATAGATACGGCCTGTGTGTGTGTGCTCAGCAGGAAGGCTGTGAGAAG
AGCCTGA MADVAGTSNRDFRGREQRLFNSEQYNYNNSKNSRPSTSLYKKAGSEPHSE
SNVPAGHTIPQVHWTKLQHSLDTALRRARSAPAAAIAARVAGQTRNITVD
PRLFKKRRLRSPRVLFSTQPPREAADTQDLDFEVGGAAPFNRTHRSKRSS
SHPIFHRGEFSVCDSVSVWVGDKTTATDIKGKEVMVLGEVNINNSVFKQY
FFETKCRDPNPVDSGCRGIDSKHWNSYCTTTHTFVKALTMDGKQAAWRFI
RIDTACVCVLSRKAVRRA*

NGF-VP3 (full length) fusion protein sequence:
ATGGAACCACACTCAGAGAGCAATGTCCCTGCAGGACACACCATCCCCCA
AGTCCACTGGACTAAACTTCAGCATTCCCTTGACACTGCCCTTCGCAGAG
CCCGCAGCGCCCCGGCAGCGGCGATAGCTGCACGCGTGGCGGGGCAGACC
CGCAACATTACTGTGGACCCCAGGCTGTTTAAAAAGCGGCGACTCCGTTC
ACCCCGTGTGCTGTTTAGCACCCAGCCTCCCCGTGAAGCTGCAGACACTC
AGGATCTGGACTTCGAGGTCGGTGGTGCTGCCCCCTTCAACAGGACTCAC
AGGAGCAAGCGGTCATCATCCCATCCCATCTTCCACAGGGGCGAATTCTC
GGTGTGTGACAGTGTCAGCGTGTGGGTTGGGGATAAGACCACCGCCACAG
ACATCAAGGGCAAGGAGGTGATGGTGTTGGGAGAGGTGAACATTAACAAC
AGTGTATTCAAACAGTACTTTTTTGAGACCAAGTGCCGGGACCCAAATCC
CGTTGACAGCGGGTGCCGGGGCATTGACTCAAAGCACTGGAACTCATATT
GTACCACGACTCACACCTTTGTCAAGGCGCTGACCATGGATGGCAAGCAG
GCTGCCTGGCGGTTTATCCGGATAGATACGGCCTGTGTGTGTGTGCTCAG
CAGGAAGGCTGTGAGAAGAGCCATGGGTCGAAAGAACATGTTTCACCATG
ATGGGTACCTTCTAGCTTTCAACTCACAACGACGATCACACACGTTACGA
CTACTAGGGCCTTTTCAGTACTTCAACTTCTCCGAGACAGATAGAGGACA
TCCATTATTTCGCCTACCTCTTAAGTATCCATCAAAAGCAATACCAGCAG
ATGAGTTAATTGACAATTTACACTAGTAACGGCGGAATAA MEPHSESNVPAGHTIPQVHWTKLQHSLDTALRRARSAPAAAIAARVAGQT
RNITVDPRLFKKRRLRSPRVLFSTQPPREAADTQDLDFEVGGAAPFNRTH
RSKRSSSHPIFHRGEFSVCDSVSVWVGDKTTATDIKGKEVMVLGEVNINN
SVFKQYFFETKCRDPNPVDSGCRGIDSKHWNSYCTTTHTFVKALTMDGKQ
AAWRFIRIDTACVCVLSRKAVRRAMGRKNMFHHDGYLLAFNSQRRSHTLR
LLGPFQYFNFSETDRGHPLFRLPLKYPSKAIPADELIDNLH*

Bombyx mori polyhedrin
sequence (GenBank acc: D37771.1):
atggcagacgtagcaggaacaagtaaccgagactttcgcggacgcgaaca
aagactattcaatagcgaacaatacaactataacaacagcttgaacggag
aagtgagcgtgtgggtatacgcatattactcagacgggtctgtactcgta
atcaacaagaactcgcaatacaaggttggcatttcagagacattcaaggc
acttaaggaatatcgcgagggacaacacaacgactcttacgatgagtatg
aagtgaatcagagcatctactatcctaacggcggtgacgctcgcaaattc
cactcaaatgctaaaccacgcgcgatccagatcatcttcagtcctagtgt
gaatgtgcgtactatcaagatggccaaaggtaacgcggtatccgtgcccg
atgagtacctacagcgatctcacccatgggaagcgaccggaatcaagtac
cgcaagattaagagagacggggaaatcgttggttacagccattacttcga
actaccccacgaatacaactccatctccctagcggtaagtggtgtacata
agaacccatcatcatacaatgtcggatcagcacataacgtaatggacgtc
ttccaatcatgcgactcggctctcagattctgcaaccgctactgggccga
actcgaattggtgaaccactacatttcgccgaacgcctacccatacctct
atatcaacaatcatagctatggagtagctctgagtaaccgtcagcgattg
ctcgtgtaa MADVAGTSNRDFRGREQRLFNSEQYNYNNSLNGEVSVWVYAYYSDGSVLV
INKNSQYKVGISETFKALKEYREGQHNDSYDEYEVNQSIYYPNGGDARKF
HSNAKPRAIQIIFSPSVNVRTIKMAKGNAVSVPDEYLQRSHPWEATGIKY
RKIKRDGEIVGYSHYFELPHEYNSISLAVSGVHKNPSSYNVGSAHNVMDV
FQSCDSALRFCNRYWAELELVNHYISPNAYPYLYINNHSYGVALSNRQRL
LV*

H1-tag sequence
MADVAGTSNRDFRGREQRLFNSEQYNYNNS

VP3-tag sequence
AFNSQRRSHTLRLLGPFQYFNFSETDRGHPLFRLPLKYPSKAIPADELID
NLH

The invention claimed is:

1. A method of differentiating cells into neurons comprising culturing the cells under static conditions in the presence of a neurotrophic growth factor gradient, wherein the gradient is generated by sustained release of the neurotrophic growth factor by a polyhedra delivery system (PODS) to set up the gradient, the PODS are in the form of microcrystals comprising polyhedrin proteins and the neurotrophic growth factor and the concentration of the neurotrophic growth factor is the highest at the PODS, and decreases with distance away from the PODS, and retains neurotrophic growth factor activity and wherein the culturing under static conditions is maintained through the differentiation process.

2. The method according to claim 1 wherein said differentiation is a cellular response to the gradient, wherein said cellular response comprises:

a) growth of cytoskeletal structural components in a defined direction relative to the direction of the gradient, and/or b) proliferation of cells up to 300 microns from the PODS, and/or c) different responses in different parts of the cell in response to different concentrations of neurotrophic growth factor caused by the gradient, due to one part of the cell being in contact with the neurotrophic growth factor at a different concentration from another part of the cell, and/or d) a different branching pattern caused by the presence of the gradient.

3. The method according to claim 2 wherein:

a) said growth is growth of microtubules/and or intermediate filaments and/or microfilaments along the direction of the gradient, and/or b) said growth is growth of microtubules/and or intermediate filaments and/or microfilaments perpendicular to the direction of the gradient, and/or c) said proliferation of cells is proportional to the concentration of neurotrophic growth factor across the gradient, and/or d) said proliferation is restricted to a concentration zone in the gradient and which extends perpendicular to the direction of the gradient, and/or e) said proliferation is proportional to the change in concentration of neurotrophic growth factor per unit distance of the gradient.

4. The method according to claim 1, wherein said differentiation comprises a change in:

(i) cell type, and/or (ii) cell shape, and/or (iii) protein expression profile.

5. The method according to claim 1, wherein:

(i) said differentiation comprises a change in the microfilament and/or intermediate filament structure, and/or (ii) said differentiation causes:

a) microfilament and/or intermediate filament growth, optionally in a direction defined by the gradient; and/or b) neurite projections at polar positions; and/or c) an unbranched chain connected by axons; and/or (iii) wherein said differentiation comprises neurite outgrowth in a direction perpendicular to the gradient.

6. The method according to claim 5, wherein the filament growth is tau and/or neurofilament growth.

7. The method according to claim 1, wherein:

said neurotrophic growth factor is attached to the polyhedrin protein, and/or said neurotrophic growth factor comprises a tag, wherein optionally said tag targets the neurotrophic growth factor for packaging within polyhedrin crystals in the PODS.

8. The method according to claim 1 wherein said neurotrophic growth factor comprises a polypeptide comprising:

(i) full length NGF according to SEQ ID NO: 1 or mature NGF according to SEQ ID NO: 2 or homologues and/or fragments thereof with at least 90% sequence identity to SEQ ID NO: 1 or SEQ ID NO: 2 that retains neurotrophic growth factor activity, and (ii) a targeting portion comprising H1 (SEQ ID NO: 3) or VP3 (SEQ ID NO: 4) or homologues and/or fragments thereof with at least 90% sequence identity to SEQ ID NO: 3 or SEQ ID NO: 4 that retain tag activity.

9. The method according to claim 1, wherein the neurotrophic growth factor is selected from the group consisting of activin, brain-derived neurotrophic factor, epidermal growth factor, basic fibroblast growth factor, glial cell derived neurotrophic factor, insulin-like growth factor 1, interleukin 6, leukaemia inhibitory factor, ephrin B2, nerve growth factor, platelet derived growth factor, transforming growth factor Beta 1, transforming growth factor Beta 3, and vasculature endothelial growth factor.

10. The method according to claim 1, wherein the growth factor is a member of the neurotrophin family.

11. The method according to claim 10, wherein the neurotrophin is selected from the group consisting of nerve growth factor (NGF), neurotrophin-3 (NT3), brain-derived neurotrophic factor (BDNF) and neurotrophin 4 (NT-4).

12. The method according to claim 1, wherein the neurotrophic growth factor is a ciliary neurotrophic factor (CNTF).

13. The method according to claim 12, wherein the CNTF is selected from the group consisting of CNTF, Leukemia inhibitory factor (LIF) and Interleukin-6 (IL-6).

14. The method according to claim 1, wherein the neurotrophic growth factor is a glial cell-line neurotrophic factor (GDNF).

15. The method according to claim 14, wherein the GDNF is selected from the group consisting of GDNF, CDNF, Artemin, Neuturin and Persephin.

16. The method according to claim 1, wherein the static conditions comprise no flow of medium.

17. The method according to claim 1, wherein the gradient persists for at least 1 day.

18. The method according to claim 1, wherein said PODS is produced in insect cells co-infected with:

a virus expressing polyhedron, and a virus expressing a neurotrophic growth factor, and wherein said insect cells are SP12 cells or said polyhedrin is *Bombyx mori* cypovirus polyhedrin or both.

* * * * *